United States Patent [19]

Lohn et al.

[11] 4,033,039

[45] July 5, 1977

[54] DENTAL HANDPIECE

[75] Inventors: Gerd Lohn, Biberach an der Riss; Anton Braun, Reute, both of Germany

[73] Assignee: Kaltenbach & Voigt, Biberach an der Riss, Germany

[22] Filed: Feb. 23, 1976

[21] Appl. No.: 660,315

[30] Foreign Application Priority Data

Mar. 10, 1975 Germany ............................ 2510384

[52] U.S. Cl. .................................................. 32/26
[51] Int. Cl.² ........................................... A61C 1/10
[58] Field of Search ............. 32/26, 27; 415/199 R, 415/503, 150, 199

[56] References Cited

UNITED STATES PATENTS 3,832,088 8/1974 Cromie .................................. 32/26

Primary Examiner—Robert Peshock

[57] ABSTRACT

A dental handpiece with clamping tongs arranged in the front end of the drive shaft to receive an insertable element. The front end of the drive shaft and the clamping tongs are axially displaceable relative to each other into an end position by actuation of a manipulator. The tongs may be displaced out of this end position by a piston arrangement.

17 Claims, 3 Drawing Figures

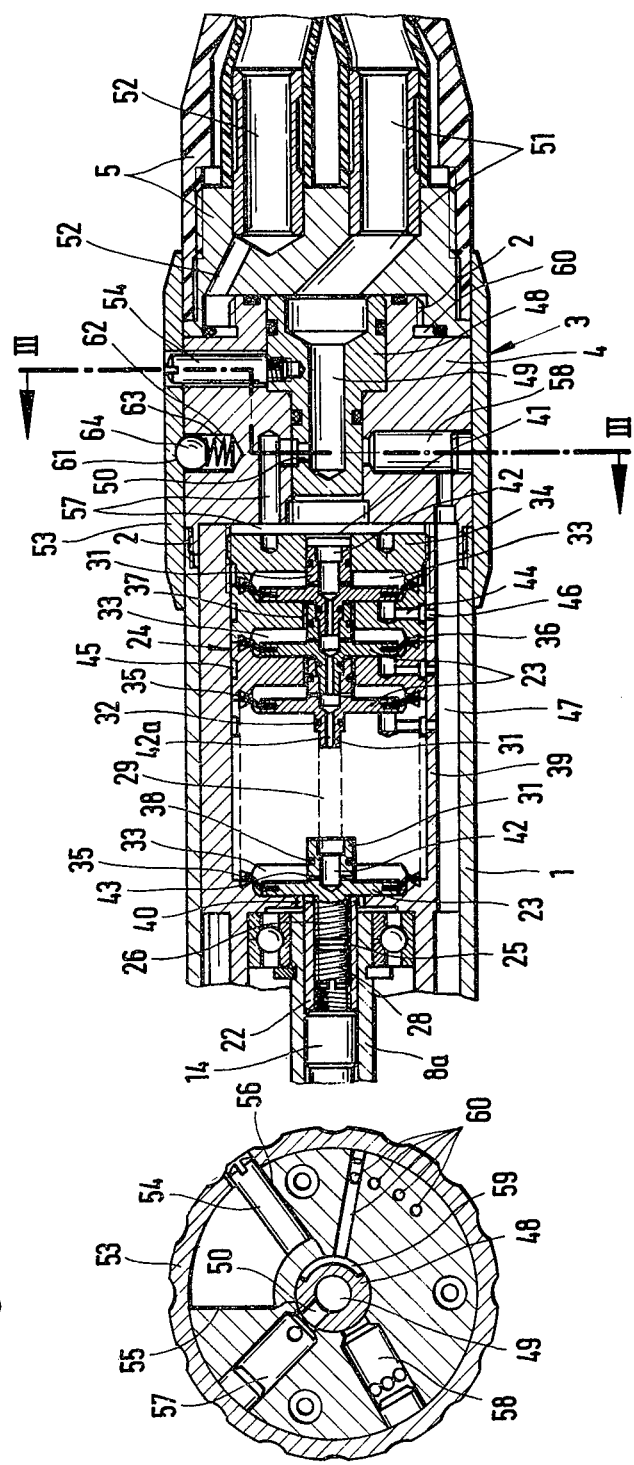

DENTAL HANDPIECE

The invention relates to a dental handpiece having clamping tongs (collet means), arranged in the front end of the drive shaft, for an insertable implement, the front end of the drive shaft and the clamping tongs being, in order to adopt the clamping position and an open position of the clamping tongs, due to actuation of manipulating means mounted at the handpiece, axially displaceable relative to each other into a movement end position and, by means of a piston arrangement arranged in the handpiece, out of the said movement end position. Such a handpiece is known from German Specification No. 2,007,754. In the case of this known handpiece, there is arranged in the front portion of the drive shaft which is designed to be hollow, rearwardly of the axially displaceable clamping tongs, a pressure member which is also axially displaceable. The clamping tongs is retained in the closure position under the action of compression spring acting indirectly on the pressure member, the influence of the compression spring on the pressure member being eliminatable by manipulating means tensioning the compression spring, in order to achieve the "open" position of the clamping tongs. concentrically arranged in the drive shaft, designed to be hollow, is a working piston influenced by the compression spring, the sealed piston stroke chamber, which is filled with pressure liquid, debouching at its end facing the pressure member into a chamber of widened cross-section and is where there is arranged sealingly relative to the chamber walls a pressure member which is axially displaceable at least with a portion of its surface and which bears with its displaceable surface at a pressure plate constituting the end of the pressure member. Thereby, unbalances are prevented also on opening and closing the clamping tongs during operation of the handpiece.

Detensioning of the implement in the clamping tongs is effected in the known handpiece by displacing the working piston which is influenced by the compression spring and which presses the pressure liquid against the pressure member which, in relationship to the piston cross-section, possesses a larger cross-section. The working piston travels, on appropriate actuation of the manipulating means being effected and under the action of the compression spring, in the direction towards the chamber possessing a cross-section which is widened relative to the piston stroke chamber, so that the pressure of the pressure liquid on the said chamber is propagated. Due to the cross-sectional enlargement of the chamber, an hydraulic force transmission takes place, so that the pressure force exerted is transmitted via the pressure member to the pressure plate and the pressure member which acts on the clamping tongs, so that the clamping tongues (divided off by slots) of the clamping tongs close about the shank of a dental implement.

It has been found that, in many cases, a still further increase of the clamping force exerted by the clamping tongs on the implement shank is desirable. Such an increase in the clamping force can, in the case of the known handpiece, be achieved only due to supplementary enlargement of the cross-section of the said chamber and of the pressure member arranged in the chamber. Such a cross-section enlargement requires an enlargement of the handpiece diameter. However, there are limits to such enlargement of the handpiece diameter, since a dental handpiece cannot, in order to prevent manipulating difficulties, be optionally enlarged as to diameter.

To this must be added the fact that the construction and functioning of the known handpiece would, on being designed for still higher pressures, become relatively complicated and costly. Thus, in particular, it is extremely difficult to master the sealing problem under extremely high pressures. For this purpose, the piston must be arranged in the piston stroke chamber to afford an entirely satisfactory seal and this applies also to the the elements influenced by the pressure liquid, since pressure liquid leakage cannot readily be replaced. Replenishment of pressure liquid is possible only by inconvenient disassembly of the handpiece. Pressure liquid leakage losses have the result that the clamping tongs is no longer able to fulfill its function.

Finally, it has been found that in consequence of the nature of the compression of the pressure liquid taking place in a known handpiece an undesirable delay in commencement of the clamping effect of the clamping tongs occurs. This delay is obviously due to the force transmission from the working piston to the pressure member which has a larger cross-section.

It is the underlying problem of the invention to provide a dental handpiece of the type mentioned at the outset which, whilst maintaining the advantage of freedom from unbalance, makes possible an increase in the clamping force of the clamping tongs, without enlarging the diameter of the handpiece and without any risk of pressure medium loss, commencement of the clamping effect of the clamping tongs taking place without delay.

For the solution of this problem, in a dental handpiece of the type mentioned at the outset, it is proposed that the piston arrangement comprises a plurality of piston-cylinder units arranged one after the other in longitudinal direction of the handpiece and subjected to the action of pressure medium, the manipulating means being connected with a control device releasing and shutting-off pressure medium supply to the piston-cylinder units.

In consequence of the fact that the piston-cylinder units constituting a "piston assembly" are arranged one behind the other, the compression force exerted by the individual pistons "adds up", so that a relatively large force is exerted on the clamping tongs operatively connected with the piston assembly. Depending on the desired magnitude of the force exerted on the clamping tongs, more or fewer piston-cylinder units can be arranged one after the other in the longitudinal direction of the handpiece, in the latter, so that it is unnecessary to employ pistons of relatively large diameter.

A possible loss of pressure medium is of no significance, since on the manipulating means being appropriately actuated pressure medium is continuously supplied from a source of pressure medium to the piston-cylinder units. The piston-cylinder units may all have uniform or substantially uniform diameter, so that no force transmission takes place, whereby the force exerted by the piston assembly acts unretarded on the clamping tongs.

A design which is space-saving and, therewith, makes possible the arrangement of a maximum number of piston-cylinder units is achieved if the piston-cylinder units have disc-like pistons arranged coaxially relative to the longitudinal axis of the handpiece and which are interconnected through the agency of their pivots and are each arranged in the cylinder chamber of a two-part cylinder housing formed with passage recesses for the piston pivots. The two-part design of the cylinder housing serves also for facilitating installation and removal of the pistons. An extremely effective form of pressure transmission from piston to piston is achieved if the pistons of the piston-cylinder units have resilient sealing sleeves projecting beyond the piston periphery and bearing fluid-tight against the wall of the cylinder housing; the sealing sleeves may be secured into gaps associated with the individual piston and available in each particular instance between two adjacent housing elements of the transversely-divided cylinder housing. The pistons then operate in diaphragm-like manner.

In order to make simple assembly possible, for example, if the piston assembly is to have more or fewer piston-cylinder units, it is proposed that the pivots of the pistons arranged one after the other shall be pushed sealingly one within the other.

Subjecting of the pistons to the action of pressure medium can be effected in simple manner if the pivots of the pistons are designed to be continuously hollow and have connecting apertures extending from the cavity formed thereby, debouching into the particular cylinder chamber, and arranged each on only one side of the piston, a passage aperture extending through the cylinder housing being associated in each particular instance with the cylinder chamber on the other piston side.

In particular if there is a pressure-resisting and traction-resisting connection between the piston assembly and the clamping tongs, and if no spring is provided for the purpose of displacing the clamping tongs into or out of one of the displacement end positions, it is for this purpose proposed that the cavities of the piston pivots, and therewith the connecting apertures of the piston pivots or the passage apertures of the cylinder housing, should be adapted to be subjected to the action of pressure medium by the control device. One for example the said connecting apertures being subjected to pressure action, the piston is displaced in one of the directions and, therewith, the clamping tongs is displaced in the direction of one of its displacement end positions. If, on the other hand, the said passage apertures are subjected to the action of pressure medium, then the pistons travel in the other direction and the clamping tongs in the direction of their other displacement end position. The said subjecting to action procedures may be effected alternatingly.

Fundamentally, the piston assembly in the case of the proposed handpiece can, in the same manner as described hereinabove with regard to the piston arrangement in the case of the known handpiece mentioned, so act on the clamping tongs that the clamping process is triggered on pressure transmission taking place to the clamping tongs. On the other hand, it is also possible, for example to correspond to the last-mentioned embodiment, to design the arrangement in such manner that, for example in the case of a fixed connection between the clamping tongs and the piston assembly, depending on the direction of subjecting to action of the pistons on the one hand the clamping procedure and on the other hand the release procedure is triggered.

In particular for making possible the triggering of the release process during the pressure transmission to the clamping tongs effected due to the piston assembly, it is proposed that the clamping tongs shall be displaceable into the clamping position under the action of a spring and into the open position under the action of the piston-cylinder units. With this arrangement, the mouth of the front end of the drive shaft preferably has a funnel-like inner cone co-operating with the longitudinally slotted end, formed with a corresponding outer cone, of the clamping tongs.

The last-mentioned embodiment makes design possible in such manner that the clamping tongs bear, at the piston disposed nearest to it, at least during the exertion of pressure on the clamping tongs, loosely against the end of the clamping tongs facing it. With this arrangement, therefore, apart from the said abutment there is no connection between the piston concerned and the clamping tongs, so that it is unnecessary to arrange the piston-cylinder units to co-rotate with the clamping tongs and therewith with the drive shaft in the handpiece, as is the case for example with the working piston of the handpiece known from the aforementioned German Specification No. 2,007,754. In a substantially simpler manner, in the case of the present embodiment, the piston-cylinder units may be arranged to be non-rotatable in the handpiece. In this case, an axially displaceably mounted pressure pusher can be arranged in the hollow drive shaft between the clamping tongs and the piston disposed nearest to the clamping tongs.

The aforementioned non-rotatable arrangement of the piston-cylinder units is in particular suitable if, according to a further embodiment, there extends between the clamping tongs and the piston disposed nearest to it, or the pressure pusher, a portion of the drive shaft which is rotatable and axially displaceable with the clamping tongs and which is constituted by the shaft of a miniature motor installed in the shaft and which may be an electrical, pneumatic or hydraulic motor. With this arrangement, expediently the rigid connection of the miniature motor shaft acting as pressure or traction rod on a clamping tongs with the clamping tongs consists in that the ends directed towards each other of the said shafts and of the clamping tongs are screwed to each other, being for example screwed one within the other.

Above all if the said miniature motor is a pneumatic or hydraulic motor, the pressure medium supplied to the handpiece for subjecting the piston-cylinder units to action and which may be a pressure liquid, for example oil or water, or a gas, for example pressure air, may in economical manner be employed simultaneously for operating the miniature motor.

The last-mentioned embodiment affords the advantageous possibility that, on actuating the manipulating means for the purpose of subjecting the piston-cylinder units to pressure medium action, in order to bring about the release (or tensioning) or "open" position of the clamping tongs, simultaneously the motor and therewith the implement clamped in the clamping tongs come to a standstill and no longer rotate, the pressure medium supply to the motor being shut-off simultaneously with the said subjecting to pressure medium action of the piston-cylinder units, by means of the manipulating means. This can be effected in especially simple manner if the control device releasing and shutting off the pressure medium supply to the piston-cylinder units comprises a control shaft mounted for rotation in the handpiece and formed with an axial inlet aperture for the pressure medium and a radial outlet aperture adapted to be connected, by rotating the control shaft, alternatingly with the cavities of the piston pivots or with the passage apertures of the cylinder housing. It is then merely necessary for the radial outlet aperture in the position of the control shaft corresponding to adoption of the clamping position of the clamping tongs to be connected with the pressure-medium-driven motor, so that on travel of the radial outlet aperture out of this position, due to appropriate rotation (change-over) of the control shaft the pressure medium supply to the motor driving the drive shaft is shutoff and the motor comes to a standstill, whereas the piston-cylinder units are so subjected to pressure medium action through the radial outlet aperture that the clamping tongs is displaced into the release (or detensioning) position. Vice versa, after taking-back of the control shaft the piston-cylinder units are so subjected to pressure medium action through the radial outlet aperture that the clamping tongs is displaced into the clamping position or this movement is effected due to the action of an above-mentioned spring. Simultaneously, in this position of the control shaft, via the radial outlet aperture thereof, the motor is subjected to the action of pressure medium, so that the clamped implement once again rotates.

If the miniature motor installed in the handpiece is an electric motor, in advantageous manner a portion of the pressure medium — in particular if the latter is pressure air — may be employed, in the clamping position of the clamping tongs, as coolant for the motor.

If the handpiece has no installed motor and the drive shaft is driven for example by a cord drive or a flexible shaft, the cord drive or the flexible shaft or the like may have associated with it a clutch which, due to the manipulating means or the control shaft, is put into the uncoupling or declutching position on actuation thereof in the sense of adoption of the release position of the clamping tongs and, vice versa, is put into the coupling position on actuation of the manipulating means in the sense of adoption of the clamping position. For this purpose, due to the action of the manipulating means a pressure medium control line acting on the clutch may be opened or closed.

Expediently, the manipulating means is constituted by a rotating ring engaging about the handpiece and connected with the control shaft by means of a radial pin.

Actuation and functioning of the manipulating means or of the control shaft are especially simple if the displacement range of the manipulating means is delimited by stops determining the two end positions of the radial outlet aperture of the control shaft, with which arrangement there is associated with one of the end positions of the outlet aperture a line path leading to the cavities of the piston pivots and with the other end position a line path leading to the passage apertures of the cylinder housing.

In order that it may in simple manner be guaranteed that, subsequent to change-over of the control shaft, the pressure medium contained in the cylinder chambers previously subjected to pressure medium action of the piston-cylinder units shall be able to escape, it is proposed that the control shaft shall have a connecting groove formed in its surface and connecting, in the end position corresponding to the connection of the radial outlet aperture with the passage apertures of the cylinder housings, the line path leading to the cavities of the piston pivots with a discharge line.

If the said end position corresponds to the clamping position of the clamping tongs in which the motor is subjected to pressure medium action, subsequent to change-over of the control shaft effective for adopting the release position of the clamping tongs, the pressure medium contained in the cylinder chambers which are now no longer subjected to pressure medium action is able to escape into a pressure medium line extending to the pressure-medium-driven motor. If, however, no pressure-medium-operated motor is provided in the handpiece, it is expedient if the control shaft is formed with a further connecting groove arranged in its surface and connecting, in the end position corresponding to connection of the radial outlet aperture with the cavities of the piston pivots, the line path extending to the passage apertures of the cylinder housing with a discharge line.

Embodiments of the invention are shown by way of example in the drawings, in which:

FIG. 2 shows, drawn to a larger scale, a detail from FIG. 1, comprising the piston-cylinder units and the control device thereof.

FIG. 3 shows a section taken along the line III—III of FIG. 2.

Figure 1:
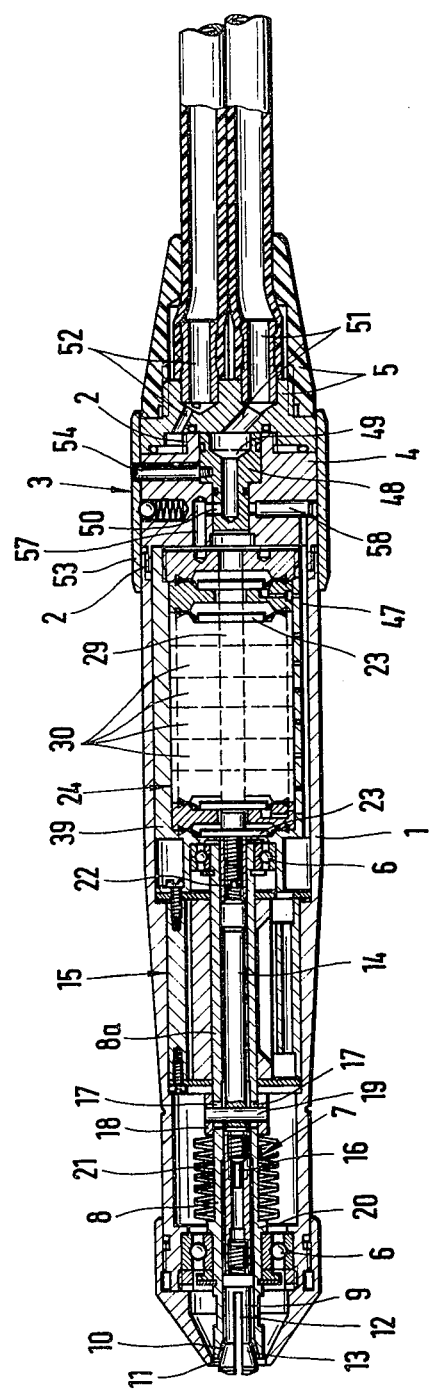
FIG. 1 shows a dental handpiece having (shown in longitudinal section) a clamping tongs disposed in the release position under the action of the piston arrangement constituted by the piston-cylinder units.

Referring to the drawings, reference numeral 1 designates the grasping sleeve of a dental handpiece connected, by screwing means 2 via an intermediate member 4 containing the control device 3, with a connecting member 5. By means of ball bearing 6, there is mounted in the grasping sleeve 1 a drive shaft 7 the front end 8 (the left-hand end in FIG. 1) of which is designed to be hollow. Arranged for axial displacement in the front end 8 of the drive shaft 7 is a clamping tongs (collet means) 9 for inserting the shank of an implement (not shown) for example a drill.

The mouth of the front end 8 of the drive shaft 7 has a funnel-like inner cone 10 co-operating with the longitudinally slotted end, having a corresponding outer cone 11, of the clamping tongs 9. The slots at the front end of the clamping tongs 9 are designated 12 and the clamping tongues formed therebetween are designated 13.

Adjacent to the clamping tongs 9 is an element 14, axially displaceable and rotatable with the clamping tongs 9, of the drive shaft 7, which is constituted by the shaft of a pressure-medium-operated miniature motor 15, preferably an air motor. The shaft element 14 is (as indicated at 16) rigidly fast with the clamping tongs 9 by screwing one within the other. Furthermore, the shaft element 14 is surrounded by a hollow shaft element 8a, rotating with it but not axially displaceable, of the front end 8 of the drive shaft 7. The one-piece hollow shaft 8, 8a is formed, in order to make possible the axial displacement taking place within it of the clamping tongs 9 together with the shaft element 14, with two diametrically oppositely located slots 17 for guiding an entrainment pin 19 extending through the shaft element 14 and having an abutment ring 18 surrounding the hollow shaft 8, 8a. Between the outer annular collar 20 of the front end 18 of the drive shaft 7 and the abutment or stop ring 18 extends a compression spring 21, preferably designed as a cup spring. A cup spring has, in advantageous manner, a constant spring characteristic line.

Adjacent the shaft element 14 is a pressure pusher 22 mounted for axial displacement in the hollow element 8a and which is not connected with the shaft element 14 and bears, at least on pressure being exerted, against the end facing it of the shaft element 14.

The pressure pusher 22 is followed by a piston 23 of a piston arrangement generally designated 24. For this purpose, the piston 23 has an extension 26 screwed into a tapped bore 25 of the pressure pusher 22. Screwed-in against the extension 26 into the tapped bore 25 is also a lock nut 28.

The piston arrangement 24 comprises a plurality of piston-cylinder units 30 arranged one after the other in the direction of the longitudinal axis 29 of the grasping sleeve 1 (FIG. 1). The pistons 23, constituting so to speak a "piston assembly", of the individual piston-cylinder units 30 are each designed in the form of a flat disc and are arranged coaxially to the longitudinal axis 29 of the grasping sleeve 1. The pistons 23 are interconnected by inserting one within the other the pivots 31 thereof, projecting out of the piston end faces. In order that this connection may be fluid-tight, the pushed-in elements of the pivots 31 have sealing rings 32. Each of the pistons 23 is arranged in a flat cylinder chamber 33 of a cylinder housing 34 divided transversely of the grasping sleeve longitudinal axis 29 and they are able to travel to and fro in the said cylinder chamber 33.

Furthermore, the pistons 23 have resilient sealing sleeves 35 projecting beyond their periphery and clamped into the gaps 36 available between two adjacent housing elements of the transversely divided cylinder housing 34. The cylinder housings 34 are formed with passage apertures 37 for the pivots 31 of the pistons 23. Also the pivot elements mounted in the passage apertures 37 are sealed, i.e. with the aid of packing rings 38.

The piston arrangement 24 constituted by the cylinder-pistons units 30 is arranged within a housing 39 provided in the grasping sleeve 1 and having at one of its (in FIG. 2 the left-hand end) an aperture 40 for the end of the hollow shaft element 8a and at its other end an aperture 41 for entry of pressure medium. Due to this arrangement, both the miniature motor 15 and also the piston arrangement 24 can be rapidly replaced, in its entirety. Due to screwing of the pressure pusher 22, it is possible to compensate for tolerances of the components disposed in the housing 39.

The pivots 31 of the piston 23 are, save for the pivot of the piston disposed nearest to the shaft element 14, designed to be hollow, with formation of continuous cavities 42, whereas the cavity 42 of the said pivot of the piston disposed nearest to the shaft element 14 is not continuously hollow but is of blind-aperture design. The cavity 42 of the pivots 31 of the remaining pistons 23 is followed by a cavity 42a which in cross-section is smaller.

The pivot elements, mounted in the passage recesses 37 of the cylinder housing 34, of the pivots 31 possess connecting apertures 43 extending from their cavity 42, debouching into the cylinder chamber 33 associated in each particular instance, and each arranged on only one side of the pistons. For the element of the cylinder chamber 33 located on the other piston side, there is formed a passage aperture 44 extending through the cylinder housing 33 and debouching in each particular instance into an outer annular duct 45 of the cylinder housing 34. Associated with each annular duct 45 is a branch line 46 extending through the housing 39. The branch lines 46 debouch into a collecting line 47 which, in the case of design of the miniature motor 15 as air motor, is simultaneously the pressure air supply line to the miniature motor and, in the case of design of the miniature motor 15 as electric motor, is the coolant supply line.

The cavities 42 of the piston pivots 31, and therewith the connecting apertures 43 of the piston pivot 31 or the passage apertures 44 of the cylinder housing 34, are adapted to be subjected to pressure medium action due to the control device 3. For this purpose, the control device 3 comprises a control shaft 48 mounted for rotation in the intermediate member 4 and formed with an axial inlet aperture 49 and a radial outlet aperture 50 for the pressure medium, the latter being adapted to be connected, by rotation of the control shaft 48, selectively via the aperture 41 of the housing 39 with the cavities 42 of the piston pivots 31 or via the collecting line 47, the branch line 46 and the annular duct 45 with the passage apertures 44 of the cylinder housing 34. Arranged in the connecting member 5 is a pressure medium supply line 51 subjected to the action of a non-visible pressure medium source and connected with the axial inlet aperture 49. Furthermore, a pressure medium discharge line 52 is arranged in the connecting member 5.

The control shaft 48 is actuatable by means of manipulating means 53 constituted by a rotating ring engaging about the handpiece and connected by means of a radial pin 54 with the control shaft 48.

The displacement range of the manipulating means 53 is delimited by stops 55, 56 (FIG. 3) determining the two end positions of the radial outlet aperture 50 of the control shaft 48, there being associated with one of the end positions of the outlet aperture 50 a line path 57, 41 extending to the cavities 42 of the piston pivots 31 and with the other end position a line path 58, 47, 46, 45 extending to the passage apertures 44 of the cylinder housing 34. The cylinder chamber 33 arranged on the left-hand side in FIG. 2 requires no passage aperture 44, since the air is able to escape through the aperture 40 to the motor chamber. As will be apparent from FIG. 3, the control shaft 48 is formed with a connecting groove 59 arranged in its surface and connecting, in the end position corresponding to connection of the radial outlet aperture 50 with the passage apertures 44 of the cylinder housing 34, the line path 57, 41 extending to the cavities 42 of the piston pivot 31 with a discharge line 60 connected with the pressure medium discharge line 52.

Furthermore, the control shaft 48 may be formed with a further connecting groove arranged in its surface and connecting, in the end position corresponding to connection of the radial outlet aperture 50 with the cavities 42 of the piston pivots 31, the line path 58, 47, 46, 45 extending to the passage apertures 44 of the cylinder housing 34 with a discharge line also connected with the pressure medium discharge line 52. If the last-mentioned end position of the manipulating means 53 — as shown in FIG. 2 in combination with FIG. 1 — corresponds to the release position of the clamping tongs, on adopting the said end position of the manipulating means 53 the pressure medium feed to element 58 of the line path 58, 47, 46, 45 is shut-off, so that no more pressure medium is supplied to a pressure-medium-operated miniature motor 15 by the collecting line 47. On commencement of the release process of the clamping tongs 9, therefore, the miniature motor 15 and therewith the shaft element 14 and also the clamping tongs 9 are immediately at a standstill.

For arresting the manipulating means 53 designed as a rotating ring, the said manipulating means is formed on its inner side with two cup-like recesses 61 arranged peripherally spaced from each other and the spacing of which corresponds to the displacement range of the manipulating means 53. Associated with the two recesses 61 is a detent or latching ball 64 mounted in a blind aperture 62 formed in the intermediate member 4, on a compression spring 63, and which in the two end positions of the radial outlet aperture 50 snaps resiliently into the recesses 61.

The design according to the invention of the handpiece makes it possible to achieve relatively small dimensioning of the handpiece, so that application thereof is possible not only as technical handpiece in the dental laboratory but also as treatment instrument in dental practice for the treatment of the living tooth.

We claim:

1. Dental handpiece, a drive shaft; manipulating means mounted in said handpiece, clamping tongs arranged in the front end of a drive shaft for an insertable implement, the front end of the drive shaft and the clamping tongs being axially displaceable relative to each other into a displacement end position by actuation of said manipulating means mounted in the handpiece, a piston arrangement, said tongs being displaceable out of the said displacement end position by means of said piston arrangement in the handpiece said piston arrangement comprising a plurality of piston-cylinder units arranged one behind the other in longitudinal direction of the handpiece and subjected to pressure medium action, a control device, said manipulating means being connected with said control device releasing and shutting-off pressure medium supply to the piston-cylinder units, spring means for holding said tongs in open position, and pressure rod means for removing the force of said spring means applied to said tongs.

2. Dental handpiece according to claim 1, wherein the piston-cylinder units have disc-like pistons arranged coaxially to the handpiece longitudinal axis and being connected with each other with their pivots, each of said pistons being arranged in the cylinder chamber of a two-part cylinder housing formed with passage apertures for the piston pivots.

3. Dental handpiece according to claim 1 wherein the pistons of the piston-cylinder units have sealing sleeves projecting beyond the piston periphery and bearing fluid-tight against the walls of the cylinder housing.

4. Dental handpiece according to claim 2 wherein the sealing sleeves are clamped into gaps associated with the individual pistons and available between in each particular instance two adjacent housing elements of the transversely-divided cylinder housing.

5. Dental handpiece according to claim 1 wherein the pivots of the pistons arranged one after the other are inserted sealingly one within the other.

6. Dental handpiece according to claim 1 wherein the pivots of the pistons are continuously hollow and are formed with connecting apertures extending from the cavity constituted thereby and debouching into a respective particular cylinder chamber, each pivot being arranged on only one side of the pistons, the cylinder chamber on the other piston side having an associated passage aperture extending through the cylinder housing.

7. Dental handpiece according to claim 6, wherein the cavities of the piston pivots and therewith the connecting apertures of the piston pivots or the passage apertures of the cylinder housing are adapted to be subjected to pressure medium action by said control device.

8. Dental handpiece according to claim 1 wherein the clamping tongs is adapted to be displaced under the influence of a spring into the clamping position and under the influence of the piston-cylinder units into the open position.

9. Dental handpiece according to claim 1 wherein the piston disposed nearest the clamping tongs bears, at least during exertion of pressure on the clamping tongs, loosely against the end facing of the clamping tongs.

10. Dental handpiece according to claim 9, wherein there is arranged between the clamping tongs and the piston disposed nearest the clamping tongs in the hollow drive shaft a pressure pusher mounted for axial displacement.

11. Dental handpiece according to claim 9 wherein there extends between the clamping tongs and the piston disposed nearest to it an element axially displaceable and rotatable with the clamping tongs of the drive shaft, said element being comprised by the shaft of a miniature motor installed in the handpiece.

12. Dental handpiece according to claim 11, wherein the miniature motor is a pressure-medium-driven motor.

13. Dental handpiece according to claim 6 wherein the control device comprises a control shaft mounted for rotation in the handpiece and formed with an axial inlet aperture of the pressure medium and a radial outlet aperture adapted to be connected by rotation of the control shaft alternatingly with the cavities of the piston pivots or with the passage apertures of the cylinder housing.

14. Dental handpiece according to claim 13, wherein the manipulating means is comprised of a rotating ring engaging about the handpiece and connected by means of a radial pin with the control shaft.

15. Dental handpiece according to claim 13 wherein the displacement range of the manipulating means is delimited by stops determining the two end positions of the radial outlet aperture of the control shaft, one of the end positions of the outlet aperture having associated with it a line path extending to the cavities of the piston pivots, and the other end position having associated therewith a line path extending to the passage apertures of the cylinder housing.

16. Dental handpiece according to claim 13 wherein the control shaft is formed with a connecting groove arranged in its surface and connecting, in the end position corresponding to connection of the radial outlet aperture with the passage apertures of the cylinder housing, the line path extending to the cavities of the piston pivots with a discharge line.

17. Dental handpiece according to claim 13 wherein the control shaft is formed with a connecting groove arranged in its surface and connecting, in the end position corresponding to connection of the radial outlet aperture with the cavities of the piston pivots, the line path extending to the passage of the cylinder housing with a discharge line.

* * * * *